(12) United States Patent
Eden

(10) Patent No.: US 6,387,706 B1
(45) Date of Patent: May 14, 2002

(54) VEHICLE MASS EMISSION MEASUREMENT

(75) Inventor: Gideon Eden, Ann Arbor, MI (US)

(73) Assignee: Sensors, Inc., Saline, MI (US)

( * ) Notice: Subject to any disclaimer, the term of this patent is extended or adjusted under 35 U.S.C. 154(b) by 0 days.

(21) Appl. No.: 09/548,448

(22) Filed: Apr. 13, 2000

Related U.S. Application Data

(60) Provisional application No. 60/129,564, filed on Apr. 16, 1999.

(51) Int. Cl.[7] .............................................. G01N 33/00
(52) U.S. Cl. ..................... 436/127; 73/118.1; 73/118.2; 73/119; 73/116; 73/23.31; 73/23.32
(58) Field of Search ................................ 436/127, 179; 702/183; 422/94; 73/23.31, 118.1, 116, 23.32, 23, 28, 863.41; 374/123

(56) References Cited

U.S. PATENT DOCUMENTS

| | | |
|---|---|---|
| 3,593,023 A | 7/1971 | Dodson et al. |
| 3,603,155 A | 9/1971 | Morris et al. |
| 3,696,247 A | 10/1972 | McIntosh et al. |
| 4,160,373 A | 7/1979 | Fastaia et al. |
| 4,341,108 A | 7/1982 | Warncke et al. |
| 4,586,367 A | 5/1986 | Lewis |
| 4,660,408 A | 4/1987 | Lewis |
| 4,727,746 A | 3/1988 | Mikasa et al. |
| 4,823,591 A | 4/1989 | Lewis |
| 5,129,257 A | 7/1992 | Carduner et al. |
| 5,184,501 A | 2/1993 | Lewis et al. |
| 5,218,857 A | 6/1993 | Decker et al. |
| 5,337,595 A | 8/1994 | Lewis |
| 5,357,113 A | 10/1994 | Liston et al. |
| 5,419,178 A | 5/1995 | Decker et al. |
| 5,423,228 A | 6/1995 | Budd et al. |
| 5,469,731 A | 11/1995 | Decker et al. |
| 5,526,122 A | 6/1996 | Intemann et al. |
| 5,546,788 A | 8/1996 | Dickow |
| 5,569,838 A | 10/1996 | Broedel et al. |
| 5,591,406 A | 1/1997 | Hirai et al. |
| 5,596,154 A | 1/1997 | Baughman |
| 5,621,166 A | 4/1997 | Butler |
| 5,639,957 A | 6/1997 | Zarchy |
| 5,739,413 A | 4/1998 | Kohn et al. |
| 5,797,682 A * | 8/1998 | Kert et al. .................. 374/123 |
| 5,929,320 A | 7/1999 | Yoo |
| 5,993,743 A * | 11/1999 | Nordman et al. ............. 422/94 |
| 6,009,742 A | 1/2000 | Balko |

(List continued on next page.)

FOREIGN PATENT DOCUMENTS

| | | |
|---|---|---|
| DE | 3923737 C2 | 12/1995 |
| EP | 0414446 A2 | 2/1991 |

OTHER PUBLICATIONS

Bureau of Mobile Sources, "New York State Department of Environmental Conservation, New York Metropolitan Area Enhanced Inspection/Maintenance Program, Technical Specifications," Dec., 1996.

Search Report from corresponding European Patent Application No. EP 98650027.0.

*Primary Examiner*—Jill Warden
*Assistant Examiner*—Brian J. Sines
(74) *Attorney, Agent, or Firm*—Van Dyke, Gardner, Linn & Burkhart, LLP

(57) ABSTRACT

A method and apparatus for measuring vehicle exhaust emission includes sampling vehicle exhaust and a dilute mixture of vehicle exhaust and ambient air. A first analyzer measures concentrations of gas components of undiluted vehicle exhaust. A second analyzer measures concentration or temperature of at least one exhaust gas component present in the dilute mixture gas component. Flow rate of the dilute mixture, the concentration and/or temperature of the at least one dilute mixture gas component and undiluted gas concentration are analyzed by a microprocessor to produce mass emissions of the vehicle exhaust gas components.

12 Claims, 4 Drawing Sheets

U.S. PATENT DOCUMENTS

| | | |
|---|---|---|
| 6,079,251 A | 6/2000 | Gaultier et al. |
| 6,085,582 A | 7/2000 | Tripathi et al. |
| 6,112,574 A * | 9/2000 | Hirano et al. ............... 73/23.31 |
| 6,112,575 A | 9/2000 | Cocconi |
| 6,128,656 A | 11/2000 | Breton |
| 6,151,952 A * | 11/2000 | Mathews et al. ........... 73/23.31 |
| 6,192,324 B1 * | 2/2001 | Lambert et al. ............. 702/183 |
| 6,200,819 B1 * | 3/2001 | Harvey et al. .............. 436/179 |

* cited by examiner

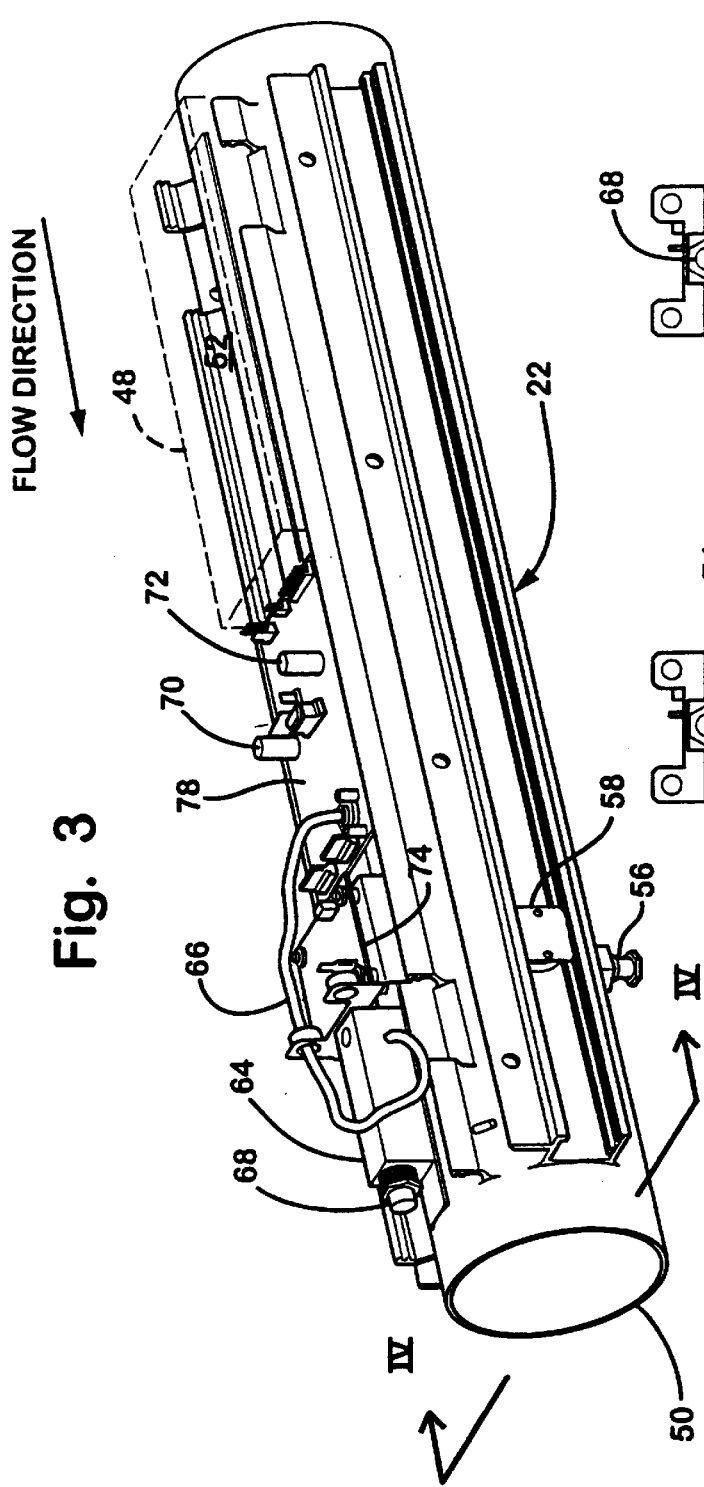
Fig. 3
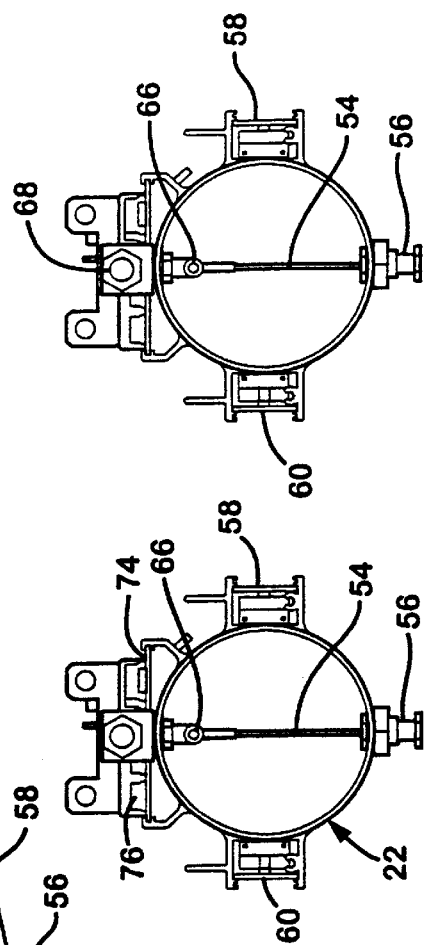
Fig. 4
Fig. 6

VEHICLE MASS EMISSION MEASUREMENT

CROSS-REFERENCE TO RELATED APPLICATION

This application claims priority from provisional patent application Serial No. 60/129,564 filed on Apr. 16, 1999.

BACKGROUND OF THE INVENTION

The present invention pertains to a method and apparatus for measuring mass emissions from a vehicle exhaust and, more particularly, to such a mass emission measurement utilizing dilution of the vehicle exhaust with air.

A vehicle exhaust emission analysis technique conventionally measures the concentrations of the component gas emissions in order to determine compliance with environmental standards. Gas concentration measurement, however, is inadequate to determine the true emissions of the vehicle. In order to measure true emissions, it is necessary to measure the mass of emissions and not just the concentration because the concentration is only one parameter of the amount of pollution generated. In order to measure mass emissions, it is necessary to also determine volume, or flow, of the exhaust gas.

One known teaching for measuring mass emission directly measures the flow of gases from the tailpipe using a technique which accounts for the operating environment. This technique is difficult to carry out because the presence of exhaust gases and high heat provides a hostile testing environment. Furthermore, an adapter must be provided which can tightly connect with a wide range of tailpipe configurations. This technique is especially difficult with dual-exhaust vehicles.

Another known technique measures concentration of exhaust gas which has been diluted. This technique requires expensive instruments because they are measuring component gas concentrations which have been diluted to very low concentrations. Furthermore, variations in exhaust gas volume causes concentration of the exhaust gases to vary, which must be taken into account in order to produce accurate results. The analyzer accuracy range must be sufficient to accommodate a low exhaust volume with a vehicle having a low pollution output as well as a high exhaust volume in a vehicle having a high pollution output. This wide sensing range adds to the expense to the instruments. Another known technique for measuring vehicle mass emission uses a carbon dioxide tracing method which determines flow rate by comparing the measured concentration of carbon dioxide in the undiluted vehicle exhaust gas with the measured concentration of carbon dioxide in a dilute mixture of exhaust gas and a diluting gas. The difficulties with such approach are two-fold. The first is that carbon dioxide is present in very low concentrations in ambient atmosphere, such as approximately 400 ppm, or 0.04%. This very low concentration of carbon dioxide in ambient air is inadequate for use in providing an accurate analyzer calibration point. When testing a vehicle, the analyzer would be operating in the single digit percent carbon dioxide range. Therefore, the use of ambient air for calibration would provide too much uncertainty at the calibration point. As a result, a source of carbon dioxide must be provided as a consumable gas in order to accurately calibrate the dilute carbon dioxide analyzer and measure dilution ratio.

The measurement of carbon dioxide in the dilute mixture of vehicle exhaust and dilution air requires filtration of the dilute mixture prior to passing the mixture over the carbon dioxide analyzer, typically a non-dispersive infrared (NDIR) analyzer, in order to remove water vapor from the dilute mixture. Such filtration requires a complicated gas-sampling system, including pumps, filters, solenoids, and the like. Without such filtration, life expectancy of the carbon dioxide sensor is reduced. However, the extra gas-sampling system adds significant cost to the analyzer. Additionally, the delay attendant to such sampling system creates a phasing between concentration measurements taken of the undiluted exhaust gas and those taken of the dilute mixture. The alignment of dilute and undiluted concentration is critical to the accuracy in the assessment of mass emissions. As the complexity of the sample system increases, the more difficult and costly it is to achieve acceptable alignment levels. As a result of cost and complexity, such technology has been practiced only in laboratory settings.

Accordingly, the need exits for a rugged, inexpensive vehicle exhaust mass emission analyzer which provides accurate measurement of vehicle mass emissions without a consumable calibration gas that can be used in laboratory and field emission testing programs.

SUMMARY OF THE INVENTION

The present invention provides a method and apparatus for measuring vehicle exhaust mass emissions which is accurate, robust, and low cost and which does not require use of a consumable calibration gas. A method of measuring vehicle exhaust mass emissions according to an aspect of the invention includes sampling undiluted vehicle exhaust and a dilute mixture of vehicle exhaust in dilution air, measuring concentration of gas components of the undiluted vehicle exhaust, measuring concentrations of a particular exhaust component of the dilute mixture and resolving the concentration of exhaust gas components, the concentration of the particular exhaust gas component, and the flow rate of a dilute mixture to mass emissions of the exhaust gas components. The processor obtains compensated values of mass exhaust gas components that are compensated for chemical reaction of the exhaust gas components. The compensated value is a function of at least one undiluted exhaust gas component and is greater than the calculated value for that component.

A vehicle exhaust mass emission analyzer, according to an aspect of the invention, includes an exhaust inlet adapted to collect vehicle exhaust and a dilution air inlet connected with the exhaust inlet to provide a dilute mixture of vehicle exhaust and dilution air. A first analyzer is provided which measures concentration of exhaust gas components from the exhaust inlet. A second analyzer is provided which measures concentration of at least one dilute mixture gas component. A meter is provided which measures flow rate of the dilute mixture. A processor resolves the concentration of the exhaust gas components, a compensated value of the concentration of the at least one dilute mixture gas component, and the flow rate of the dilute mixture to mass emissions of the exhaust gas components. The compensated value is adjusted for chemical reaction of the exhaust gas components and is greater than the uncompensated value.

The present invention provides a method and apparatus for measuring vehicle exhaust mass emissions which is accurate, robust, and low cost and which does not require use of a consumable calibration gas. A method of measuring vehicle exhaust mass emissions according to an aspect of the invention includes measuring the temperatures of the ambient air, undiluted vehicle exhaust, and the dilute mixture of the vehicle exhaust in dilution air, measuring concentration of gas components of the undiluted vehicle exhaust, and measuring flow rate of the dilute mixture. The method further includes resolving the concentration of exhaust gas components, the three temperatures, and the flow rate of a dilute mixture to mass emissions of the exhaust gas components. This may be accomplished using temperature balance equations to determine actual dilution ratio. From the actual dilution ratio and dilute mixture volume, exhaust volume can be determined. From exhaust gas volume and measured exhaust gas component concentrations, exhaust mass emissions can be accurately determined.

A vehicle exhaust mass emission analyzer, according to an aspect of the invention, includes an exhaust inlet adapted to collect vehicle exhaust and a dilution air inlet connected with the exhaust inlet to provide a dilute mixture of vehicle exhaust and dilution air. A first analyzer is provided which measures concentration of exhaust gas components from the exhaust inlet. A second analyzer is provided which measures the temperatures of the non-diluted vehicle exhaust, the ambient dilution air and the diluted exhaust component. A meter is provided which measures flow rate of the dilute mixture. A processor resolves the concentration of the exhaust gas components, the three temperatures, and the flow rate of the dilute mixture to mass emissions of the exhaust gas components.

These and other objects, advantages, and features of this invention will become apparent upon review of the following specification in conjunction with the drawings.

BRIEF DESCRIPTION OF THE DRAWINGS

FIG. 3 is a perspective view of a dilute mixture duct useful with the invention;

FIG. 4 is a view from IV—IV in FIG. 3;

FIG. 6 is the same view as FIG. 4 of the alternative embodiment.

DESCRIPTION OF THE PREFERRED EMBODIMENT

Figure 1:
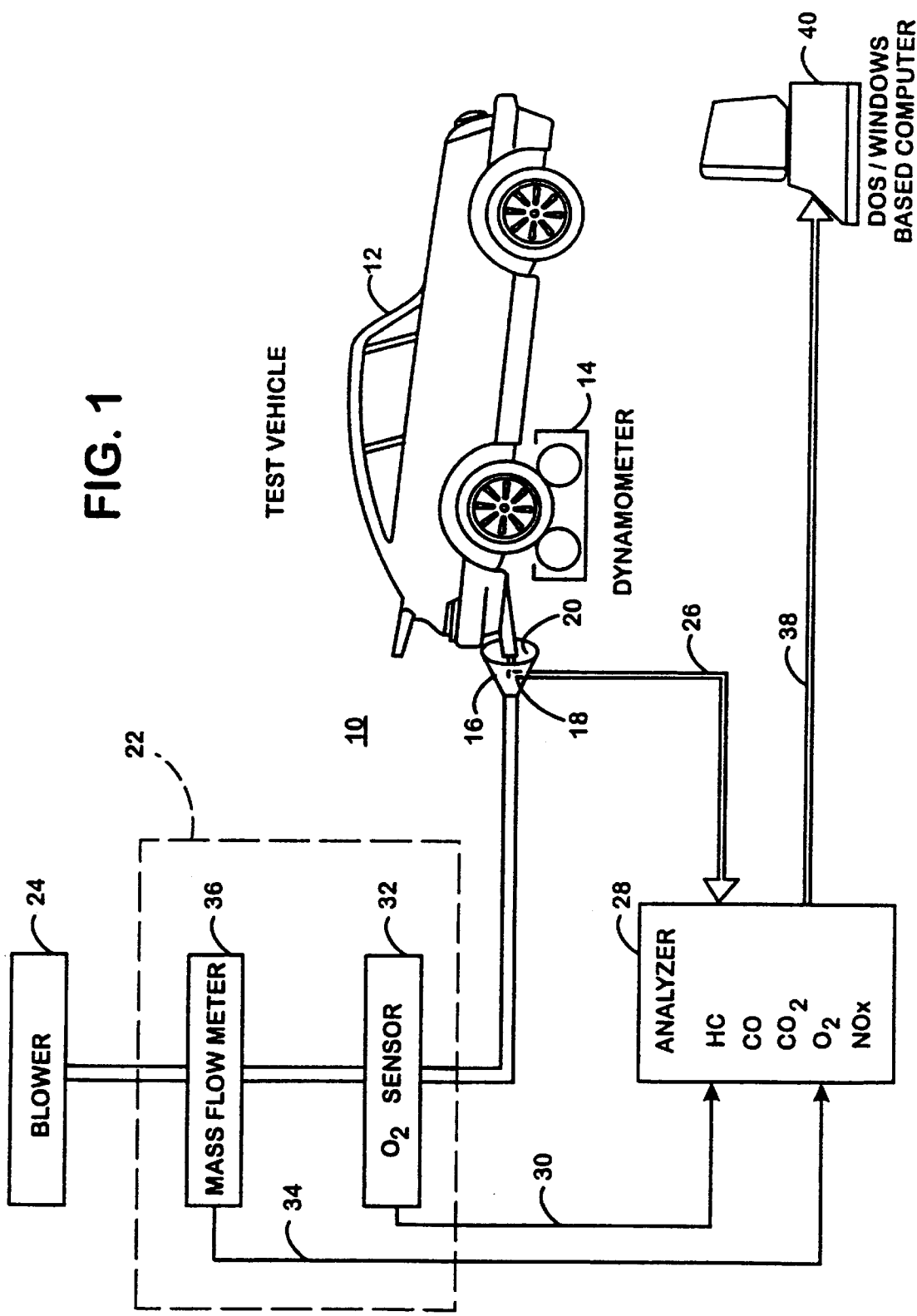
FIG. 1 is a flow diagram of a method of measuring vehicle exhaust mass emission and a vehicle exhaust mass emission analyzer, according to the invention.
Figure 2:
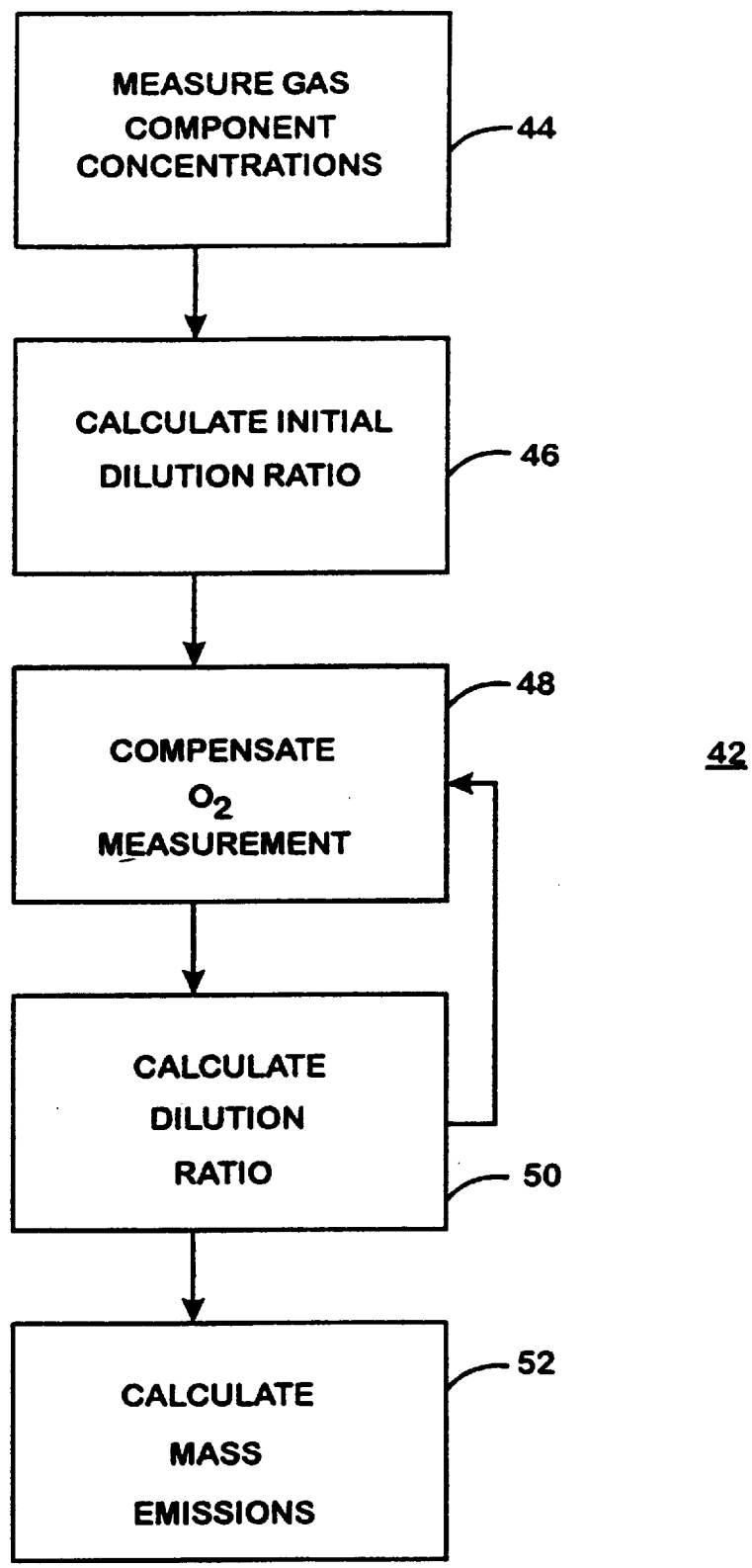
FIG. 2 is a flowchart of an iterative process for compensating for chemical interaction between oxygen and exhaust gas components.

Referring now specifically to the drawings, and the illustrative embodiments depicted therein, a vehicle exhaust mass emission analyzer and method 10 is illustrated measuring mass emissions of a vehicle 12 with the operating condition of the vehicle optionally being monitored by a dynamometer 14 (FIG. 1). A sampling assembly, or cone, 16 has an exhaust inlet 18 configured to interface with a vehicle exhaust pipe and sample undiluted exhaust gases emitted by the vehicle. Concentric with the exhaust inlet is an ambient air inlet 20 which draws ambient air from the environment outside of the vehicle. A dilute mixture duct 22 receives a diluted mixture of vehicle and exhaust dilution air induced into the duct by a blower 24.

A gas-sampling system 26 samples undiluted exhaust gas from exhaust inlet 18 and supplies gas samples to a gas concentration analyzer 28. Gas analyzer 28 measures gas concentration in the exhaust gas which may utilize principles disclosed in commonly assigned U.S. Pat. No. 5,510, 269 issued to Black et al. for an INFRARED METHOD AND APPARATUS FOR MEASURING GAS CONCENTRATION INCLUDING ELECTRONIC CALIBRATION, the disclosure of which is hereby incorporated herein by reference. Analyzer 28 additionally receives an input 30 from a gas analyzer 32 which detects the concentration of a component gas in dilute mixture duct 22 as will be explained in more detail below. Preferably, gas analyzer 32 is an oxygen sensor for reasons that will be set forth in more detail below. Analyzer 28 additionally receives an input 34 from a mass flow meter 36. Mass flow meter 36 is positioned in dilute mixture duct 22, and is configured to present a low impedance on the vehicle exhaust and provides a measure of dilute mixture flow rate. Analyzer 28 includes an output 38 which is provided to a computer 40 for displaying and performing various pass/fail indications for vehicle 12 based upon mass emission measurements outputted from analyzer 28.

In order to determine mass emission of each component gas in the exhaust vehicle 12, hydrocarbon (HC), carbon monoxide (CO), carbon dioxide ($CO_2$), oxygen ($O_2$), and oxides of nitrogen ($NO_x$), it is necessary to determine both the volume of the exhaust and the concentration of each component gas. Concentration of each component gas is measured directly by analyzer 28. Exhaust gas volume $V_e$ is determined as the product of dilute mixture volume $V_d$, measured by mass flow meter 36, and a dilution ratio (d). Using this information, the mass of each component gas can be determined according to equation 1:

$$\text{Mass} \times \text{Density} \times \text{Volume} \times \text{Concentration} = PVC \quad (1)$$

The mass of the dilute mixture is equal to the mass of its components for any individual or any combination of the emitted components of the exhaust gas.

$$M_d = M_e + M_a \quad (2)$$

where:

$M_d$=Mass of the diluted mixture;

$M_e$=Mass of the exhaust; and $M_a$=Mass of ambient.

Likewise, the volume of the dilute mixture is equal to the volume of its components.

$$V_d = V_e + V_a \quad (3)$$

where:

$V_d$ is volume of dilute mixture;

$V_e$ is volume of undiluted exhaust; and $V_a$ is volume of ambient.

Combining equations 2 and 3 results in:

$$P_d V_d C_d = P_e V_e C_e + P_a C_a (V_d - V_e) \quad (4)$$

where:

$P_d$, $P_a$, and $P_e$ are the density coefficients;

$C_d$ is measured concentration of oxygen in the dilute mixture;

$C_a$ is measured concentration of oxygen in ambient air; and $C_e$ is measured concentration of oxygen in the undiluted vehicle exhaust.

Solving for volume of the exhaust results in:

$$V_e = V_d \frac{(P_d C_d - P_a C_a)}{(P_e C_e - P_a C_a)} \quad (5)$$

The value of $C_d$ is measured by oxygen analyzer 32. The value of $C_e$ is measured by analyzer 28. The value of $C_a$ may be measured by either analyzer 28 or analyzer 32, or both, when sampling assembly 16 is disconnected from the vehicle 12, such as between vehicle tests when only ambient air is being drawn in sampling assembly 16.

From the above, it can be seen that mass emissions of each of the component gases of the vehicle exhaust can be measured by the combination of analyzer 28, analyzer 32, and mass flow meter 34. In the illustrated embodiment, analyzer 32 is a zirconium oxide oxygen sensor. Such sensors are commercially available at auto parts stores and are marketed by many different manufacturers. Zirconium oxide oxygen sensors operate at an elevated temperature, such as 700 degrees centigrade. At such elevated temperatures, the oxygen in the dilute mixture of vehicle exhaust and dilution air combine with molecules of carbon monoxide and hydrocarbon, which are also present in the dilute mixture. This chemical interaction, which may include combustion, between oxygen and other component gases in the vehicle exhaust would introduce error in the mass emission calculations unless appropriate compensation is made. Measurement of oxygen in a dilute mixture of vehicle exhaust in dilution air is quite complicated. Fast-responding oxygen sensors operate at elevated temperatures, such as 700 degrees centigrade. Such elevated temperatures result in chemical reactions between oxygen and several exhaust gases. As a result, residual dilute concentration can be less than the measured oxygen. Without compensation, such chemical would adversely affect the mass emission measurement accuracy.

Analytical compensation can be provided for some of the exhaust components, specifically the carbon monoxide and hydrocarbons. The following formulas describe such reactions:

$$2CO + O2 \rightarrow 2CO2 \quad (6)$$

$$C3H8 + 5O2 \rightarrow 4H2O + 3CO2 \quad (7)$$

$$2C6H14 + 19O2 \rightarrow 14H2O + 12CO2 \quad (8)$$

From these equations, it is indicated that for every two molecules interacting with oxygen, one oxygen molecule is depleted and, for every reduced hydrocarbon (propane) molecule, five oxygen molecules are depleted, etc. Therefore, it is possible to provide compensation based upon these predictive reactions by measuring and computing the diluted carbon monoxide and representatives of hydrocarbon components, and assuming certain efficiency of the chemical reactions. In order to provide compensation, a compensation algorithm 42 is performed. Compensation algorithm 42 begins by measuring gas component concentrations at 44 utilizing analyzer 32 and exhaust gas analyzer 28.

A dilution ratio is calculated ignoring the chemical reactions at 46 and utilized to compensate oxygen measurement made by analyzer 32 for reduction in oxygen molecules resulting from chemical interaction with other component gases at 48. After the measured concentration of oxygen is compensated at 48, a new dilution ratio is calculated at 50. The new dilution ratio calculated at 50 is utilized to compensate the oxygen concentration measurement at 48 and to produce a new dilution ratio at 50. This process is interactively carried out until the algorithm is determined to converge utilizing known mathematical techniques. After a dilution ratio is determined at 50, the mass emissions of the vehicle are calculated at 52. Alternatively, the iterative conveyance can be modeled and stored in a look-up table or constants in an equation.

It has been experimentally found that under maximal chemical reaction calculated efficiencies, the measured oxygen was much lower than the maximal predictive value. In other words, the depleted oxygen was always higher than the predictive values. Actual loss of oxygen can be as much as twice the predictive value when measuring it with diluted exhaust components.

In order to provide better compensation algorithm, the following approach was applied. Varying concentrations of diluted exhaust gas components were generated utilizing a multiplicity of vehicles operating under varying loading conditions. Consequently, the generated data included multi-dimensional parameters related to various combinations of exhaust component concentrations. The generated exhaust gases were simultaneously measured by an elevated temperature oxygen sensor and a galvanic oxygen sensor. The difference between the two sensors was recorded and correlated to the concentration of the various gas components. Once the statistical multiple correlation coefficients were calculated, the following correction formula was applied:

$$O2(\text{actual loss}) = O2(\text{predicted loss}) + Ki * Ci \quad (9)$$

Where:
Ci are the diluted exhaust gas concentrations, and
Ki are the statistical multiple correlation coefficients.

The value of Ki depends on the actual configuration of the sampling system including the geometry of the system, and the temperature of the oxygen sensor.

Oxygen sensor 32 may sample dilute mixture from dilute mixture duct 22 utilizing various techniques. In one technique, the oxygen sensor is placed in the duct in order to measure oxygen directly from the air flowing through duct 22. In another embodiment, a proportionalizer system, such as a pitot tube, is utilized to sample a fixed proportion of the gas flowing through duct 22. In this embodiment, oxygen sensor 32 is placed in the portion of the diluted mixture drawn from duct 22. This embodiment is preferred because the reduced flow of dilute mixture over the oxygen sensor reduces the amount of heat dissipation caused by the dilute mixture flowing over the oxygen sensor thereby allowing the oxygen sensor to operate at its design temperature. Other sampling techniques will suggest themselves to those skilled in the art.

A detailed embodiment of dilute mixture duct 22 is illustrated in FIGS. 3 and 4 in which directing flow of dilute mixture gas is illustrated by the arrow in FIG. 3. Blower 24, which is not illustrated in FIGS. 3 and 5, would be connected at the left end of dilute mixture duct 22 as viewed in FIG. 3.

Dilution duct 22 includes a tubular housing 50 which may provide an option area 52 for mounting the sample tube assembly 48 of analyzer 28 and gas sampler 26. A vortex strut 54 is supported within housing 50 by a strut holder 56. An ultrasonic transmitter 58 and ultrasonic receiver 60 are mounted to housing 50 on opposite sides of strut 54. As will be explained in more detail below, vortex strut 54, ultrasonic transmitter 58 and ultrasonic receiver 60 in combination make up mass flow meter 36.

A gas diverter, or pitot tube 62, samples dilute mixture flowing through housing 50. The sampled gas is conveyed to an oxygen measurement chamber 64 by a tube 66. An oxygen sensor 68 is positioned in chamber 64. Pitot tube 62, oxygen measurement chamber 64, tube 66 and oxygen sensor 62 make up analyzer 32.

Dilute mixture duct 22 further includes a temperature sensor 70 and pressure sensor 72, both of which sense conditions in the interior of housing 50. A flow electronic circuit board 74, which may include a microprocessor control circuit, receives inputs from ultrasonic receiver 60 and calculates mass flow volume. A processor circuit board 76, which preferably includes a microprocessor control circuit, performs the analysis function of gas analyzer 28 and produces output 38.

In the illustrated embodiment, mass flow meter 36 is a flow meter system which is commercially available from J-TEC Associates of Cedar Rapids, Iowa which has been modified to meet the requirements of the present application. Mass flow meter 36 operates by transmitting an ultrasonic signal by ultrasonic transmitter 58 which is sensed by ultrasonic receiver 60. The signal passes around strut 54 and is modified by air turbulence created by the dilute mixture flowing past strut 54. The amount of turbulence created is proportional to dilute mixture flow rate. Therefore, by processing the signal received by ultrasonic receiver 60, in a manner which would be apparent to the skilled artisan, dilute mixture flow rate can be calculated.

Oxygen sensor 68 is preferably a model GMS-10 zirconium oxide sensor marketed by Philips. The oxygen sensor is preferably operated according the principles disclosed in the application guide entitled "Dynamic ZrO2 oxygen sensors for improved combustion control," published by Gasmodul, a Honeywell Company, the disclosure of which is hereby incorporated herein by reference.

Figure 5:
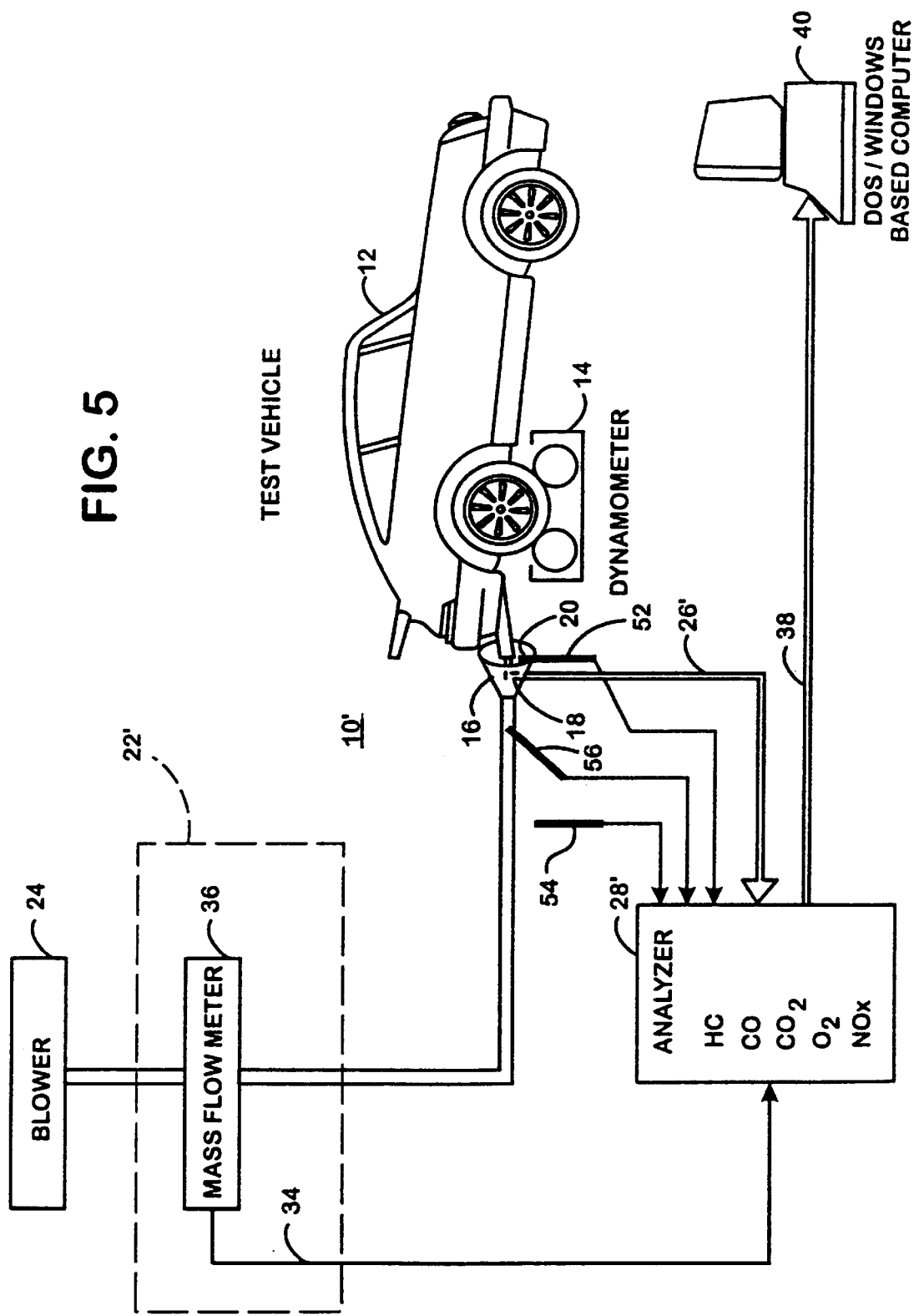
FIG. 5 is the same view as FIG. 1 of an alternative embodiment.

An alternative vehicle exhaust mass emission analyzer and method 10' has a gas sampling system 26' that samples undiluted exhaust gas from exhaust inlet 18 and supplies gas samples to a gas concentration analyzer 28 (FIGS. 5 and 6). Analyzer 28' additionally receives data from three temperature probes 52, 54 and 56. Probe 54 measures the ambient temperature. Probe 52 measures the temperature of the non-diluted exhaust gas. Probe 56 is located in the path of the diluted gas and measures its temperature. Analyzer 28' additionally receives an input 34 from a mass flow meter 36. Mass flow meter 36 is positioned in dilute mixture duct 22, and is configured to present a low impedance on the vehicle exhaust and provides a measure of dilute mixture flow rate. Analyzer 28' includes an output 38 which is provided to a computer 40 for displaying and performing various pass/fail indications for vehicle 12 based upon mass emission measurements outputted from analyzer 28'.

In order to determine mass emission of each component gas in the exhaust vehicle 12, hydrocarbon (HC), carbon monoxide (CO), carbon dioxide ($CO_2$), and oxides of nitrogen ($NO_x$), it is necessary to determine both the volume of the exhaust and the concentration of each component gas. Concentration of each component gas is measured directly by analyzer 28. Exhaust gas volume $V_e$ is determined as the product of dilute mixture volume $V_d$, measured by mass flow meter 36, and a dilution ratio (d). Using this information, the mass of each component gas can be determined according to equation 1:

$$\text{Mass} = \text{Density} \times \text{Volume} \times \text{Concentration} = PVC \qquad (1)$$

The mass of the dilute mixture is equal to the mass of its components for any individual or any combination of the emitted components of the exhaust gas.

$$M_d = M_e + M_a \qquad (2)$$

where:
$M_d$=Mass of the diluted mixture;
$M_e$=Mass of the exhaust; and
$M_a$=Mass of ambient air.

Assuming that the heat capacities of all gas components are identical, it follows that:

$$M_e(T_e - T_d) = M_a(T_d - T_a) \qquad (10)$$

where:
$T_e$ is the temperature of undiluted exhaust;
$T_d$ is the temperature of the dilute mixture; and
$T_a$ is the ambient temperature.

Combining equations 2 and 3 results in:

$$M_e(T_e - T_d) = (T_d - T_a)(M_d - M_e) \qquad (11)$$

Assuming identical density coefficients of all gas components, it follows that:

$$M_e = M_d \frac{T_d - T_a}{T_e - T_a} \qquad (12)$$

The value of $T_d$ is measured by the temperature probe 56, $T_a$ is measured by probe 54 and $T_e$ is measured by probe 52. From the above, it can be seen that mass emissions of each of the component gases of the vehicle exhaust can be measured by the combination of analyzer 28', temperature probes 52, 54, and 56, and mass flow meter 34. In the illustrated embodiment, the temperature probes can be thermistors, RTDs or thermocouple devices. Such sensors are commercially available and are marketed by many different manufacturers.

The structure of the mass flow meter is illustrated in FIG. 6. The dilution duct 22 includes a vortex strut 54 which is supported by a strut holder 56. An ultrasonic transmitter 58 and ultrasonic receiver 60 are mounted on opposite sides of strut 54. As will be explained in more detail below, vortex strut 54, ultrasonic transmitter 58 and ultrasonic receiver 60 in combination make up the mass flow meter.

A flow electronic circuit board 74, which may include a microprocessor control circuit, receives inputs from ultrasonic receiver 60 and calculates mass flow volume. A processor circuit board 76, which preferably includes a microprocessor control circuit, performs the analysis function of gas analyzer 28 and produces output 38.

The present invention is both relatively inexpensive and robust in operation. This is achieved because only one gas-sampling system is required for measurement of the concentrations of the component gases of the vehicle exhaust. A separate gas-sampling system is not required for the oxygen sensor. Such oxygen sensor is readily available, inexpensive and adapted to operating in a harsh environment. Additionally, calibration of the system can be performed using ambient air. This is because oxygen comprises a large enough component of ambient air to provide a reading which is within the acceptable level of accuracy of even a moderately accurate instrument, such as, say, one percent (1%). Therefore, the requirement for a consumable calibration gas is eliminated. Importantly, the present invention provides exceptionally accurate readings of mass emissions of the vehicle irrespective of the operating conditions of the vehicle.

Changes and modifications in the specifically described embodiments can be carried out without departing from the principles of the invention, which is intended to be limited only by the scope of the appended claims, as interpreted according to the principles of patent law including the Doctrine of Equivalents.

The embodiments of the invention in which an exclusive property or privilege is claimed are defined as follows:

1. A method of measuring vehicle exhaust mass emission, comprising:
   sampling undiluted vehicle exhaust and a dilute mixture of vehicle exhaust and ambient air;
   measuring concentrations of undiluted gas components of said vehicle exhaust;
   measuring the temperatures of the undiluted exhaust gas, the dilute mixture and the ambient air;
   measuring flow rate of said dilute mixture; and
   resolving said concentration of undiluted exhaust gas components, said temperatures and said flow rate of said dilute mixture to mass emissions of said exhaust gas components.

2. The method of claim 1 wherein said resolving includes compensating the heat loss of said dilute mixture to the ambient temperature.

3. The method of claim 1 wherein said resolving said concentration of undiluted exhaust gas components, said temperatures and the flow rate of said dilute mixture to the mass of said exhaust gas components includes:

$$M_e = M_d \frac{T_d - T_a}{T_e - T_a}$$

where:
   $M_e$ is mass of the exhaust;
   $M_d$ is mass of the dilute mixture;
   $T_d$ is measured temperature of the dilute mixture;
   $T_a$ is measured temperature of ambient air; and
   $T_e$ is measured temperature of the vehicle exhaust gas.

4. The method of claim 1 wherein said sampling undiluted vehicle exhaust and a dilute mixture of vehicle exhaust and ambient air includes providing an exhaust inlet adapted to collect vehicle exhaust and a dilution air inlet connected with said exhaust inlet to provide a dilute mixture of vehicle exhaust and dilution air.

5. The method of claim 1 wherein said measuring concentrations of undiluted gas components includes providing a gas analyzer which measures concentration of undiluted exhaust gas components from said exhaust inlet.

6. The method of claim 1 wherein said measuring the temperatures of the undiluted gas, the dilute mixture and the ambient air includes providing a temperature analyzer which measures the temperatures of the vehicle exhaust gases, the dilution air and said dilute mixture of vehicle exhaust and dilution air.

7. The method of claim 6 wherein said temperature analyzer comprises temperature probes.

8. The method of claim 7 wherein said temperature probes are selected from a group consisting of thermistors, RTDs and thermocouple devices.

9. The method of claim 1 wherein said measuring flow rate includes providing a meter which measures flow rate of said dilute mixture.

10. The method of claim 1 wherein said resolving includes providing a processor which resolves said concentration of the undiluted exhaust gas components and said temperatures to mass of the exhaust gas components.

11. The method of claim 10 wherein said processor compensates heat loss of said dilute mixture resulting from the temperature difference between said dilute mixture and the ambient air.

12. The method of claim 1 wherein said sampling undiluted vehicle exhaust and a dilute mixture of vehicle exhaust and ambient air includes providing a blower for propelling the dilute mixture of exhaust and dilution air.

* * * * *